United States Patent [19]

Goddard

[11] Patent Number: 4,794,072
[45] Date of Patent: Dec. 27, 1988

[54] PHOSPHATE ESTER STABILIZERS

[75] Inventor: John D. Goddard, Harrow, United Kingdom

[73] Assignee: Eastman Kodak Company, Rochester, N.Y.

[21] Appl. No.: 159,794

[22] Filed: Feb. 24, 1988

[30] Foreign Application Priority Data

Mar. 18, 1987 [GB] United Kingdom ............... 8706358

[51] Int. Cl.$^4$ .............................................. G03C 1/34
[52] U.S. Cl. .................................... 430/546; 430/551; 430/610; 430/613
[58] Field of Search ................ 430/551, 546, 610, 613

[56] References Cited

U.S. PATENT DOCUMENTS

| 4,324,856 | 4/1982 | Kawakatsu et al. | 430/610 |
|---|---|---|---|
| 4,326,022 | 4/1982 | Ito et al. | 430/546 |
| 4,661,440 | 4/1987 | Tschopp et al. | 430/551 |
| 4,749,645 | 7/1988 | Goddard et al. | 430/551 |

Primary Examiner—Paul R. Michl
Assistant Examiner—Lee C. Wright
Attorney, Agent, or Firm—Harold E. Cole

[57] ABSTRACT

A photographic element comprising a support having thereon at least one silver halide emulsion layer having associated therewith a yellow or cyan dye-forming coupler and a dye stabilizer comprising a phosphate ester compound having the formula:

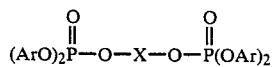

wherein
each Ar independently represents a substituted or unsubstituted arcyl group, and
X is a linking group.

9 Claims, No Drawings

PHOSPHATE ESTER STABILIZERS

This invention relates to the stabilization of dye images produced in photographic materials. More particularly, it relates to the use of certain phosphate ester compounds as stabilizers for improving the stability of dye images obtained by color developing coupler-incorporated photographic silver halide materials.

A common form of color photographic material comprises red-, green- and blue-sensitive silver halide emulsion layers in or adjacent to which are incorporated cyan-, magenta- and yellow-dye forming couplers, respectively. On development of such a material with a developer containing p-phenylenediamine color developing agent, the oxidation product produced on reduction of the silver halide by the developing agent reacts with the appropriate coupler to give image dye.

The dye image obtained by color development can deteriorate as a result of the action of light, heat and/or humidity and various measures are known for reducing such deterioration. U.S. Pat. No. 4,326,022 describes the use of high boiling organophosphorus coupler solvents which are said to improve the resistance of developed dye images to such deterioration. While dye stabilization can be achieved in this way, it is desirable to be able to improve dye stability without putting any restriction on the coupler solvent employed.

The present invention provides phosphate ester compounds which can be incorporated in a color photographic material to improve yellow and cyan dye stability independently of the coupler solvent used, and which can be prepared easily and at a low cost. The compounds confer improved stability on image dyes without causing adverse effects such as fogging, deterioration in color hue and poor dispersion or crystal formation. The compounds used in the present invention are either viscous, colorless liquids which may be employed as or as part of the coupler solvent or crystalline, colorless solids which may be employed as addenda.

A satisfactory level of dye stability in a photographic material may require, singly or in combination, the use of an excess of coupler above the level necessary for image formation and the use of a low level of coupler solvent. Such undesirable measures may be overcome by using a stabilizer compound employed in the present invention which permits the use of less coupler and an increase in the ratio of coupler solvent to coupler.

According to the present invention there is provided a photographic element comprising a support having thereon at least one silver halide emulsion layer having associated therewith a yellow or cyan dye-forming coupler and a dye stabilizer comprising a phosphate ester compound having the formula:

$$(ArO)_2\overset{O}{\underset{\|}{P}}-O-X-O-\overset{O}{\underset{\|}{P}}(OAr)_2$$

wherein
each Ar independently represents a substituted or unsubstituted aryl group, and
X is a linking group.

Examples of suitable aryl groups include phenyl and naphthyl groups. Preferred substituted aryl groups include 4-substituted phenyl groups such as 4-alkyl substituted phenyl.

In a preferred embodiment of the invention, the linking group X contains from about 2 to about 40 carbon atoms.

In another preferred embodiment, X is the residue of a polyhydroxy compound. Optionally, the linking group has one or more diaryl phosphate groups in addition to those shown in the general formula.

In yet another preferred embodiment, the linking group is alkylene (e.g., methylene, hexamethylene, etc.), alkylidene, arylene, alkylenebisarylene, alkylidenebisarylene, sulfonylbisarylene or cycloalkylenebisalkylene, said groups being optionally substituted.

With reference to the general formula, specific examples of compounds suitable for use in the present invention are as follows:

| Compound | Ar | X |
|---|---|---|
| 1 | H₃C—⟨phenyl⟩— | —(CH₂)₆— |
| 2 | H₃C—⟨phenyl⟩— | —⟨phenyl⟩—C(CH₃)₂—⟨phenyl⟩— |
| 3 | ⟨phenyl⟩— | —(CH₂)₄ |
| 4 | ⟨phenyl⟩— | —(CH₂)₆— |
| 5 | ⟨phenyl⟩— | —(CH₂)₁₀— |
| 6 | ⟨phenyl⟩— | 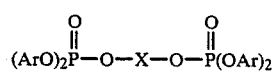 |
| 7 | ⟨phenyl⟩— | —⟨phenyl⟩—SO₂—⟨phenyl⟩— |
| 8 | i-C₃H₇—⟨phenyl⟩— | —(CH₂)₄— |
| 9 | i-C₃H₇—⟨phenyl⟩— | —(CH₂)₆— |
| 10 | i-C₃H₇—⟨phenyl⟩— | —⟨phenyl⟩—C(CH₃)₂—⟨phenyl⟩— |
| 11 | i-C₃H₇—⟨phenyl⟩— | —CH₂—⟨phenyl⟩—CH₂— |

| Com- pound | Ar | X |
|---|---|---|
| 12 | 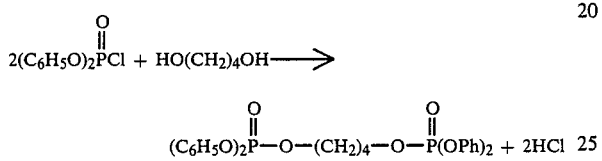 | $-CH_2$ $CH_2-$ <br> $\diagdown$ $\diagup$ <br> C <br> $\diagup$ $\diagdown$ <br> $CH_2$ $CH_2$ <br> $\mid$ $\mid$ <br> $(C_6H_5O)_2P-O$ $O-P(OC_6H_5)_2$ <br> $\parallel$ $\parallel$ <br> O O |

The phosphate ester compounds are readily prepared by reacting an appropriate diaryl chlorophosphate with an appropriate polyhydroxy compound. Many suitable starting materials are commercially available. For example, the preparation of compound 3 may be represented as follows:

$$2(C_6H_5O)_2\overset{\overset{O}{\parallel}}{P}Cl + HO(CH_2)_4OH \longrightarrow$$

$$(C_6H_5O)_2\overset{\overset{O}{\parallel}}{P}-O-(CH_2)_4-O-\overset{\overset{O}{\parallel}}{P}(OPh)_2 + 2HCl$$

The phosphate ester compounds are used in an amount sufficient to stabilize the photographic image dyes and their pressure, e.g., in an amount from about 0.1 to about 2.0 moles per mole coupler, more preferably from about 0.5 to about 1.0 mole per mole coupler.

Because the compound is used as a dye stabilizer, it is incorporated in the coupler-containing layer or a layer adjacent thereto. It can be incorporated as a separate dispersion, but is preferably incorporated in admixture with the coupler. Both coupler and stabilizer may be dissolved in a conventional coupler solvent, such as dibutyl phthalate. As in the production of ordinary coupler dispersions, a volatile and/or water-miscible auxiliary solvent, such as ethyl acetate, may be used to aid the dispersion process and then removed by evaporation or by washing the set dispersion. Also, the dispersion process can be assisted by the presence of a surface active compound, as usual in the manufacture of coupler dispersions.

In the following discussion of suitable materials for use in the emulsions and elements of this invention, reference will be made to *Research Disclosure*, December 1978, Item 17643, published by Industrial Opportunities Ltd., The Old Harbourmaster's, 8 North Street, Emsworth, Hants P010 7DD, U.K., the disclosures of which are incorporated herein by reference. This publication will be identified hereafter as "*Research Disclosure*". References giving information on couplers and on methods for their dispersions are given in Sections VII and XIV, respectively, of *Research Disclosure*.

The couplers commonly employed in photographic materials are water-insoluble compounds often containing ballast groups, phenolic (including naphtholic) couplers being used for producing cyan dyes and compounds containing an activated methylene group, including both heterocyclic and open-chain compounds, being used for producing yellow and magenta dyes. Important yellow couplers are benzoylacetanilides and important magenta couplers are pyrazolones. Patents describing couplers include the following U.S. Pat. Nos.:

| Cyan dye-forming | |
|---|---|
| 3,367,531 | 3,034,892 |
| 2,423,730 | 3,311,476 |
| 2,474,293 | 3,419,390 |
| 2,772,826 | 3,458,315 |
| 2,895,826 | 3,476,563 |
| Yellow dye-forming | |
| 2,298,443 | 3,277,155 |
| 2,407,210 | 3,408,194 |
| 2,875,057 | 3,415,652 |
| 2,908,573 | 3,447,928 |
| 3,265,506 | 3,933,501 |
| Magenta dye-forming | |
| 2,343,703 | 3,062,653 |
| 2,369,489 | 3,127,269 |
| 2,600,788 | 3,311,476 |
| 2,908,573 | 3,419,391 |
| 2,933,391 | 3,518,429 |

An account of dye-forming development is given in "Modern Photographic Processing", Vol. 2, Grant Haist, Wiley, New York, 1978, Chapter 9.

The stabilizers are useful in any coupler-incorporated silver halide photographic materials, including monochrome materials, false-color materials and color transparency, negative and print materials, to stabilize the image dye obtained on development with a solution including a p-phenylenediamine color developing agent. Such developing agents are well-known, being described in, for example *Photographic Processing Chemistry*, L. F. A. Mason, Focal Press, London, 2nd edition (1975), pp. 229-235 and *Modern Photographic Processing*, Grant Haist, Wiley, New York (1979), Volume 2, pp. 463-8.

The silver halide emulsion employed in the elements of this invention can be either negative-working or positive-working. Suitable emulsions and their preparation are described in *Research Disclosure* Sections 1 and II and the publications cited therein. Suitable vehicles for the emulsion layers and other layers of elements of this invention are described in *Research Disclosure* Section IX and the publications cited therein.

The photographic elements of this invention or individual layers thereof, can contain brighteners (see *Research Disclosure* Section V), antifoggants and stabilizers (see *Research Disclosure* Section VI), antistain agents and image dye stabilizer (see *Research Disclosure* Section VII, paragraphs I and J), light absorbing and scattering materials (see *Research Disclosure* Section VII), hardeners (see *Research Disclosure* Section XI), plasticizers and lubricants (see *Research Disclosure* Section XII), antistatic agents (see *Research Disclosure* Section XIII), matting agents (see *Research Disclosure* Section XVI) and development modifiers (see *Research Disclosure* Section XXI).

The photographic elements can be coated on a variety of supports as described in *Research Disclosure* Section XVII and the references described therein.

Photographic elements can be exposed to actinic radiation, typically in the visible region of the spectrum, to form a latent image as described in *Research Disclosure* Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Examples of the preparation of a stabilizer compound used in the present invention are as follows:

PREPARATIVE EXAMPLE 1

Preparation of 4,4′-Isopropylidenebisphenylbis[bis(4-methylphenyl)-phosphate]

Bis(4-methylphenyl)phosphorochloridate (29.7 g, 0.1 mole) was added dropwise to a solution of 4,4′-isopropylidenebisphenol (11.4 g, 0.05 mole) in pyridine (200 ml) with stirring at room temperature. The mixture was stirred for 3 hours as pyridinium hydrochloride was precipitated. The reaction mixture was poured into ice/water (1.5 l) and neutralized with concentrated hydrochloric acid. The mixture was extracted into ethyl acetate, dried (MgSO$_4$) and evaporated to dryness under vacuum. The resulting viscous oil was dissolved in dichloromethane and filtered through a bed of silica. Evaporation of the solvent under vacuum afforded the product as a viscous, colorless oil (86% yield).

$C_{43}H_{42}O_8P_2$ requires: C, 69.0; H, 5.7; P, 8.3. Found: C, 69.4; H, 5.4; P, 7.5%.

The structure and purity of the compound were further confirmed by mass spectrum, n.m.r., high performance liquid chromatography (h.p.l.c.) and thin layer chromatography (t.l.c.).

PREPARATIVE EXAMPLE 2

Preparation of Hexamethylenebis[bis(4-isopropylphenyl)-phosphate]

Bis(4-isopropylphenyl)phosphorochloridate (70.6 g, 0.2 mole) was added dropwise with stirring to a solution of hexane-1,6-diol (11.8 g, 0.1 mole) in dry pyridine (350 ml). The mixture was stirred for 5 hours then poured into ice/water (2 l) and neutralized with concentrated hydrochloric acid. The aqueous layer was decanted from the viscous product which was then dissolved in dichloromethane, dried (MgSO$_4$) and filtered through a bed of silica. Evaporation of the solvent under vacuum afforded the product as a viscous, colorless oil (78% yield).

$C_{42}H_{56}O_8P_2$ requires: C, 67.2; H, 7.5; P, 8.3. Found: C, 66.8; H, 7.3; P, 8.0%.

The structure and purity of the compound were further confirmed by mass spectrum, n.m.r., h.p.l.c. and t.l.c.

PREPARATIVE EXAMPLE 3

Preparation of Tetramethylenebis(diphenylphosphate)

Diphenylphosphorochloridate (53.6 g, 0.2 mole) was added dropwise to a stirred solution of 1,4-butanediol (9.0 g, 0.1 mole) in dry pyridine (400 ml). After 3 hours stirring the mixture was poured into ice/water (2 l) and neutralized with concentrated hydrochloric acid. The solid product was filtered off, dried under vacuum and recrystallized from ethyl acetate to give a colorless, pure solid, m.p. 105° C. (80% yield).

$C_{28}H_{28}O_8P_2$ requires: C, 60.7; H, 5.1; P, 11.2. Found: C, 60.7; H, 5.1; P, 10.9%.

The structure and purity of the compound were further confirmed by mass spectrum, n.m.r., h.p.l.c. and t.l.c.

The invention is further illustrated in the following Examples.

EXAMPLE 1

A number of phosphate ester compounds were tested as addenda in a photosensitive layer containing a yellow dye-forming coupler. Strips were prepared by coating corona-treated, polyethylene-coated paper supports with a photosensitive layer containing a silver bromoiodide emulsion at 0.38 g/m$^2$ silver, gelatin at 1.36 g/m$^2$ and dispersions of Coupler I in dibutyl phthalate as the coupler solvent (1.5 moles per mole of coupler) and the phosphate ester (0.5 mole per mole of coupler). The coupler coverage was 0.83 millimole/m$^2$. The photosensitive layer was overcoated with a layer containing gelatin at 3.0 g/m$^2$ and bisvinylsulfonylmethyl ether hardener at 1.0 weight percent based on total gelatin.

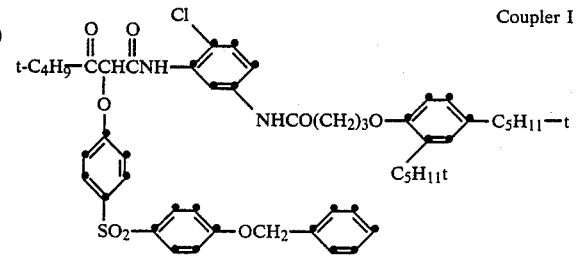

Coupler I

Samples were exposed through a graduated-density test object and developed with 4-amino-3-methyl-N-ethyl-N-$\beta$-(methanesulphonamido)-ethylaniline in a standard Ektaprint-2 process (see British Journal of Photography Annual 1986, pages 37 and 38).

The samples so obtained were faded for six weeks using a 5.4 Klux xenon source, the ultraviolet component of which was removed using a coating of Tinuvin 328 (Ciba-Geigy) in a gelatin dispersion at a coverage of 750 g/m$^2$. Fade was monitored by status A reflection densitometry measurements.

The results are given in Table 1 below.

TABLE 1

| Stabilizer Compound | Original Density | Density Loss After Fade Test | |
|---|---|---|---|
| | | Dens. Units | (%) |
| None (Control) | 1.00 | −0.15 | −15 |
| 6 | 1.00 | −0.08 | −8 |
| 4 | 1.00 | −0.08 | −8 |
| 2 | 1.00 | −0.14 | −14 |
| 3 | 1.00 | −0.11 | −11 |
| 10 | 1.00 | −0.07 | −7 |
| 9 | 1.00 | −0.08 | −8 |
| 12 | 1.00 | −0.07 | −7 |
| None (Control) | 2.37 | −1.23 | −52 |
| 6 | 2.47 | −0.81 | −33 |
| 4 | 2.51 | −0.85 | −34 |
| 2 | 2.49 | −1.11 | −44 |
| 3 | 2.52 | −0.90 | −36 |
| 10 | 2.44 | −0.46 | −19 |
| 9 | 2.49 | −0.53 | −21 |

TABLE 1-continued

| Stabilizer Compound | Original Density | Density Loss After Fade Test | |
|---|---|---|---|
| | | Dens. Units | (%) |
| 12 | 2.50 | −0.66 | −26 |

The results show that the presence of the stabilizer compounds of the invention considerably improved the stability of the yellow image dye.

EXAMPLE 2

A number of phosphate ester compounds were tested as coupler solvents. Strips were prepared and tested as in Example 1 except that the phosphate ester being tested replaced the dibutyl phthalate and the weight of the phosphate ester used was 0.46 that of the coupler.

A control strip was prepared and tested in which dibutyl phthalate was the coupler solvent.

The results are given in Table 2 below.

TABLE 2

| Stabilizer Compound | Original Density | Density Loss After Fade Test | |
|---|---|---|---|
| | | Dens. Units | (%) |
| None (Control) | 1.00 | −0.15 | −15 |
| 6 | 1.00 | −0.05 | −5 |
| 10 | 1.00 | −0.05 | −5 |
| 9 | 1.00 | −0.06 | −6 |
| 12 | 1.00 | −0.06 | −6 |
| None (Control) | 2.37 | −1.23 | −52 |
| 6 | 2.36 | −0.25 | −11 |
| 10 | 2.39 | −0.17 | −7 |
| 9 | 2.38 | −0.24 | −10 |
| 12 | 2.42 | −0.21 | −9 |

Use of the phosphate ester stabilizer compounds of the invention markedly improved the dye stability.

EXAMPLE 3

Strips were prepared in accordance with Example 2 except that the photosensitive layer was coated on polyethylene terephthalate supports instead of paper. The strips were exposed, developed and faded in accordance with Example 2 except that the fade time was 360 hours.

Fade was assessed by U.V./visible spectrophotometry using the loss in absorption density at the wavelength of maximum absorption as a measure of the fade.

The results are given in Table 3 below.

TABLE 3

| Stabilizer Compound | Original Density | Density Loss After Fade Test | |
|---|---|---|---|
| | | Dens. Units | (%) |
| None (Control) | 1.00 | −0.52 | −52 |
| 6 | 1.03 | −0.17 | −16 |
| 10 | 0.96 | −0.06 | −6 |
| 9 | 1.02 | −0.10 | −10 |
| 12 | 0.95 | −0.14 | −15 |

The stabilizer compounds of the invention are shown to improve the stability of the dye image.

EXAMPLE 4

Compound 9 was tested as an addendum in a photosensitive layer containing a cyan dye-forming coupler.

A monochrome control strip was prepared by coating a corona-treated, polyethylene-coated paper support with a photosensitive layer containing a silver bromoiodide emulsion at 0.27 g Ag/m², gelatin at 1.52 g/m² and Coupler II at 0.66 g/m² dispersed in dibutyl phthalate coupler solvent at 0.33 g/m². The photosensitive layer was overcoated with a layer containing gelatin at 3.0 g/m² and bisvinylsulfonylmethyl ether hardener at 1.5 weight percent based on total gelatin.

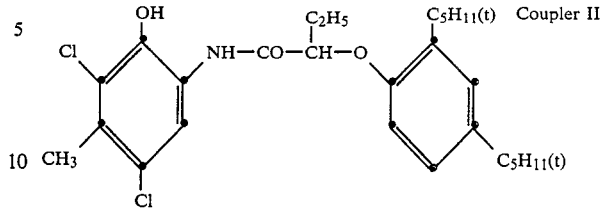

A second coating was prepared as above except that an amount of the test compound 9 equimolar to the coupler was also incorporated into the coupler dispersion.

Samples were exposed through a graduated density test object and processed through a standard Ektaprint-2 process.

Separate samples of both the processed coatings were incubated for 3 weeks in a wet oven (60° C., 70% relative humidity) and a dry oven (75° C.). The following results were obtained:

TABLE 4

| | Wet Oven Test | | |
|---|---|---|---|
| Stabilizer Compound | Original Density | Density Loss After Fade Test | |
| | | Dens. Units | (%) |
| None (Control) | 1.00 | −0.11 | −11 |
| 9 | 1.00 | −0.06 | −6 |
| None (Control) | 1.70 | −0.26 | −15 |
| 9 | 1.70 | −0.19 | −11 |

TABLE 5

| | Dry Oven Test | | |
|---|---|---|---|
| Stabilizer Compound | Original Density | Density Loss After Fade Test | |
| | | Dens. Units | (%) |
| None (Control) | 1.00 | −0.34 | −34 |
| 9 | 1.00 | −0.15 | −15 |
| None (Control) | 1.70 | −0.65 | −38 |
| 9 | 1.70 | −0.26 | −15 |

The above results clearly show improvements in the stability of the cyan image dye when the stabilizer according to the invention is incorporated.

The invention has been described in detail with particular reference to preferred embodiments thereof, but it will be understood that variations and modifications can be effected within the spirit and scope of the invention.

What is claimed is:

1. A photographic element comprising a support having thereon at least one silver halide emulsion layer having associated therewith a yellow or cyan dye-forming coupler and a dye stabilizer comprising a phosphate ester compound having the formula:

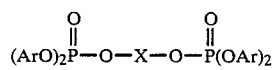

wherein
each Ar independently represents a substituted or unsubstituted aryl group, and
X is a linking group.

2. The element of claim 1 wherein Ar is phenyl or naphthyl.

3. The element of claim 1 wherein the linking group X contains from about 2 to about 40 carbon atoms.

4. The element of claim 1 wherein the linking group X is the residue of a polyhydroxy compound.

5. The element of claim 1 wherein the linking group X is a substituted or unsubstituted alkylene, alkylidene, arylene, alkylenebisarylene, alkylidenebisarylene, sulfonylbisarylene or cycloalkylenebisalkylene group.

6. The element of claim 1 wherein the phosphate ester compound is present in an amount from about 0.1 to about 2.0 moles per mole coupler.

7. The element of claim 1 wherein the phosphate ester compound is a liquid which is present as or as part of a coupler solvent.

8. The element of claim 1 wherein the phosphate ester compound is a solid which is dissolved in a coupler solvent.

9. The element of claim 8 wherein the coupler solvent comprises dibutyl phthalate.

* * * * *